US006949266B2

(12) United States Patent
Schachter et al.

(10) Patent No.: US 6,949,266 B2
(45) Date of Patent: Sep. 27, 2005

(54) HYDROPHILIC, LUBRICIOUS MEDICAL DEVICES HAVING CONTRAST FOR MAGNETIC RESONANCE IMAGING

(75) Inventors: Deborah Schachter, Edison, NJ (US); You-Ling Fan, Warren, NJ (US); Venceslav Rutar, Flemington, NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 111 days.

(21) Appl. No.: 10/362,203
(22) PCT Filed: Apr. 17, 2001
(86) PCT No.: PCT/US01/12458
§ 371 (c)(1), (2), (4) Date: Feb. 21, 2003
(87) PCT Pub. No.: WO02/22186
PCT Pub. Date: Mar. 21, 2002

(65) Prior Publication Data
US 2004/0058082 A1 Mar. 25, 2004

Related U.S. Application Data
(60) Provisional application No. 60/231,601, filed on Sep. 11, 2000.

(51) Int. Cl.[7] .............................. B05D 1/38; B05D 3/02
(52) U.S. Cl. ..................... 427/2.24; 427/127; 427/128; 427/131; 427/160; 427/407.1
(58) Field of Search ................................ 427/2.1, 2.24, 427/127, 128, 131, 160, 402, 407.1

(56) References Cited

U.S. PATENT DOCUMENTS

| 5,091,205 A | 2/1992 | Fan ............................... 427/2 |
| 5,731,087 A | 3/1998 | Fan et al. .................... 428/412 |

FOREIGN PATENT DOCUMENTS

| WO | 94/08629 | 4/1994 | .......... A61K/49/00 |
| WO | 94/23782 | 10/1994 | .......... A61M/25/01 |
| WO | 99/60920 | 12/1999 | ........... A61B/49/00 |

OTHER PUBLICATIONS

Fan. Y. L., "Hydrophilic Lubricity in Medical Applications," *Encyclopedia Handbook of Bioengineering*, vol. 2, pp. 1331–1345.

Jinkins, J. R., et al., "Proton Relaxation Enhancement Associated with Iodinated Contrast Agents in MR Imaging of the CNS," *American Journal of Neuroradiology*, vol. 13, 1992, pp. 19–27.

*Primary Examiner*—Erma Cameron

(57) ABSTRACT

Disclosed are medical devices having lubricious coatings which are capable of producing magnetic resonance image in the presence of a suitable magnetic field. The medical devices are easy to manipulate in body channels because of reduced friction with tissue surfaces and can be readily visualized in real time, which greatly facilitates the tracking of the medical devices while present within the bodies of humans or animals. The level of magnetic susceptible agent in the coatings of medical devices can be easily controlled by the present invention to give the desired performance. Coating processes to produce these medical devices are also disclosed.

18 Claims, 4 Drawing Sheets

SEM-EDS (15 KV, 5000X) of uncoated specimen. The three peaks between 4.5 and 5.2 kev are associated with the barium filler in the stent and the three peaks between 6 and 7.1 kev correspond to Gd.

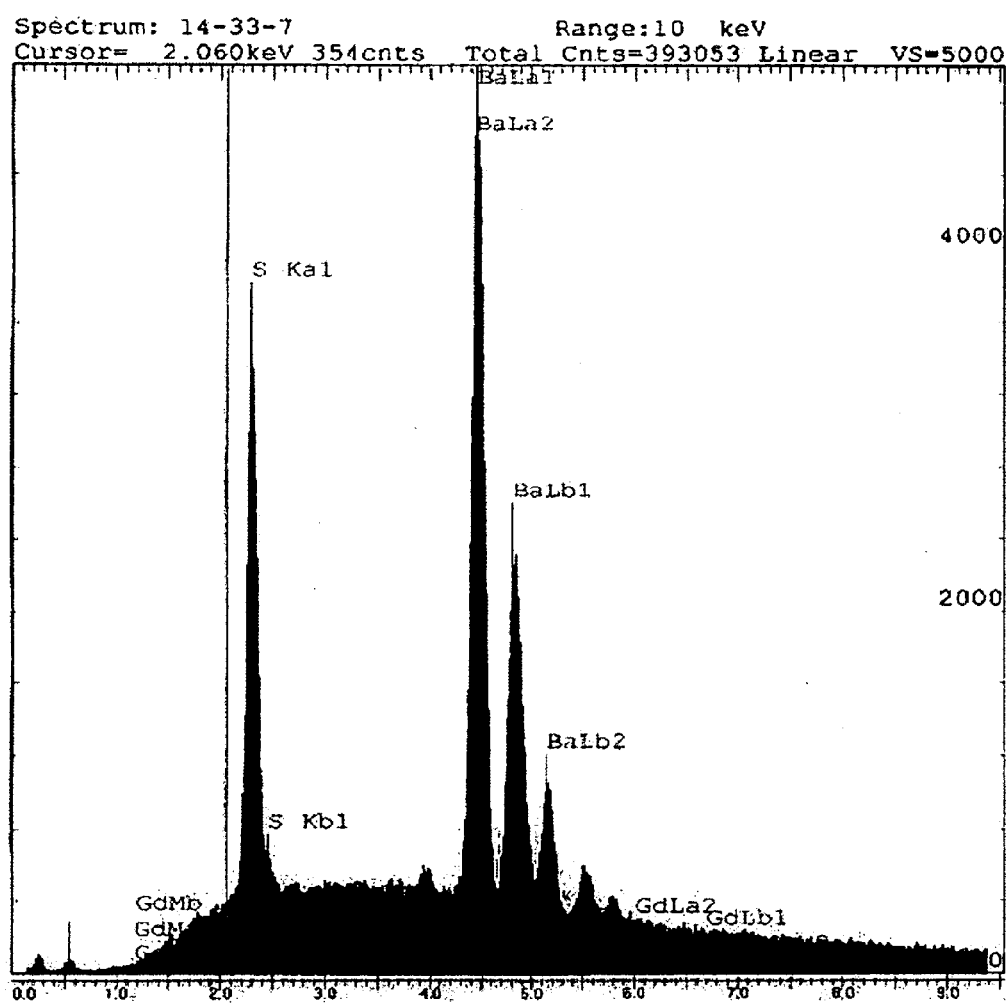
Figure 1a: SEM-EDS (15 KV, 5000X) of uncoated specimen. The three peaks between 4.5 and 5.2 kev are associated with the barium filler in the stent and the three peaks between 6 and 7.1 kev correspond to Gd.

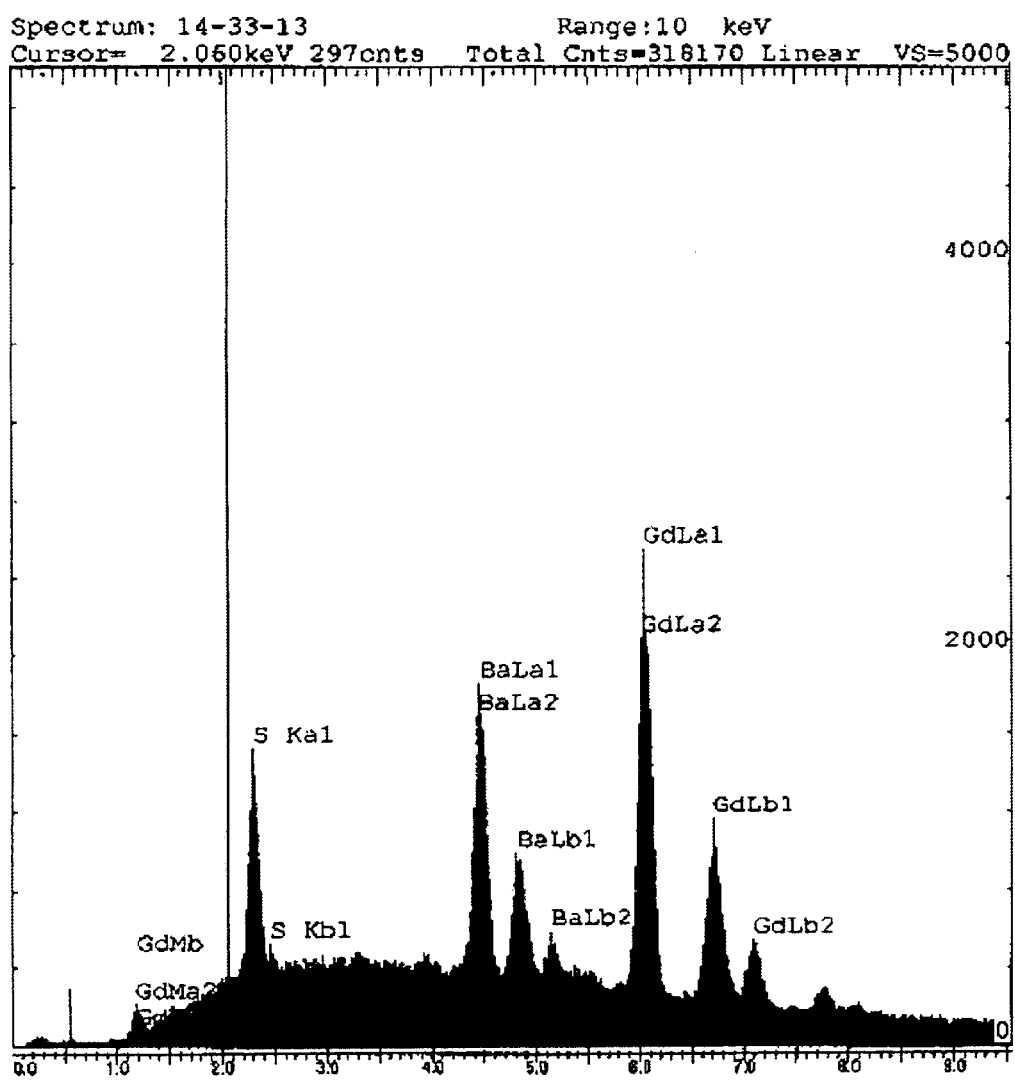
Figure 1b: SEM-EDS (15 KV, 5000X) of coated specimen. The three peaks between 4.5 and 5.2 kev are associated with the barium filler in the stent and the three peaks between 6 and 7.1 kev correspond to Gd.

Figure 2: Scanning electron micrograph (15 kV and 1000X) of cross-section of guidewire after soaking in $GdCl_3$ / DMF solution at 50°C for 30 minutes. The lighter areas are Gd as determined by the elemental analysis feature of the SEM.

Figure 3: Scanning electron micrograph (1.2 kv and 3000X) of cross-section of guidewire that has been coated with the gadolinium complex and subsequently coated with a cellulose acetate. Note the two layers on the edge of the sample. The inner is the Gd coating and the outer is the cellulose acetate coating.

HYDROPHILIC, LUBRICIOUS MEDICAL DEVICES HAVING CONTRAST FOR MAGNETIC RESONANCE IMAGING

This application claims the benefit of provisional application No. 60/231,601, filed Sep. 11, 2000.

FIELD OF THE INVENTION

The present invention relates to hydrophilic lubricious coatings for medical devices that can be detected by magnetic resonance imaging.

BACKGROUND OF THE INVENTION

A variety of lubricious coatings have been proposed for use on the surfaces of medical devices such as, for example, catheters, guide wires, endotracheal tubes and implants. Common materials used in the art to provide lubricious coatings for medical devices include, for example, oil, silicone, and polymeric materials, such as poly(N-vinylpyrrolidone), hydrophilic polyurethanes, Teflon, poly(ethylene oxide) and poly(acrylic acid). Among the most common materials used to provide lubricious coatings are hydrophilic polymers which are covalently bonded to the substrate with a binder polymer having reactive functional groups, e.g., isocyanate, aldehyde, and epoxy groups. Other binder polymers comprise, for example, copolymers containing a vinyl moiety. Details of such coatings are disclosed, for example, in U.S. Pat. Nos. 5,091,205 issued Feb. 25, 1992 and 5,731,087 issued Mar. 24, 1998.

Medical device coatings that are visible in magnetic resonance imaging (MRI) provide the opportunity to use magnetic resonance to perform therapeutic procedures. The possible uses of image guided therapy otherwise known as interventional MR are extensive. Examples of these applications include monitoring ultrasound and laser ablations, guiding the placement of biopsy needles, endovascular therapy, and visualizing disease, such as tumors, interoperatively. This type of interventional therapy eliminates the hazards of ionizing radiation associated with x-ray fluoroscopy. At the same time, it acquires real-time images in three dimensions and due to the sensitivity of the MR to the test tissue environmental it can also provide additional diagnostic information. As used herein, the term "real-time" means that the visualization of the medical device is synchronized with the movement of the device in the body of the patient.

MRI shares the same underlying theory as nuclear magnetic resonance (NMR). Contrast is obtained when water protons in of the test tissue have shorter relaxation times relative to the protons of other water molecules in the environment around the tissue. Contrast can be enhanced by the presence of an agent that can shorten the relaxation time of water protons even further. Such agents operate in the following manner. When protons are pulsed with a radio-frequency pulse in a magnetic field, their nuclear dipoles are a certain angle out of phase with the applied magnetic field. Longitudinal relaxation is the drift back of the protons back to their original alignment with the magnetic field. Paramagnetic contrast agents facilitate this relaxation process by accommodating the excess energy from the protons caused by the pulsing. Gadolinium has become the paramagnetic ion most often used in the art because it has the largest number of unpaired electrons in the 4f orbitals and therefore exhibits the greatest longitudinal ($T_1$) relaxivity of any element. In the presence of gadolinium, some of the magnetic energy of the nuclei in the high-energy state can transfer energy to gadolinium and the gadolinium can accept this energy because of its magnetic susceptibility.

Alternatively, contrast in magnetic resonance is also commonly achieved using super-paramagnetic particles. Typically, iron oxide nanoparticles are used because can they enhance the rate of the spin-spin or $T_2$ (transverse) relaxation. This is accomplished in the following way. After a 90° radio-frequency pulse in the x direction, a magnetization component appears in the y direction. This can be pictured as the nuclear dipoles bunched together and precessing around the surface of a double cone transverse to the applied magnetic field. This condition is called phase coherence. Super-paramagnetic particles cause inhomogeneities in the applied magnetic field resulting in different effective magnetic fields for each of the nuclei. These inhomogeneities cause the nuclei to lose phase coherence at a faster rate relative to proton nuclei that are not in the presence of super-paramagnetic particles.

In order to detect medical devices in using MRI, gadolinium complexes have been grafted onto the surface of polymer substrates. For example, in PCT patent application publication number WO 99/60920, there is disclosed a magnetic resonance (MR) signal-emitting coating which includes a paramagnetic metal ion-containing polymer complex and a method of visualizing medical devices in magnetic resonance imaging, which includes the step of coating the devices with the paramagnetic-ion containing polymer. The patent application further discloses a coating for visualizing medical devices in magnetic resonance imaging, comprising a complex of formula (I):

$$P\text{-}X\text{-}L\text{-}M^{n+} \qquad (I)$$

Wherein P is a polymer, X is a surface functional group, L is a chelate, M is a paramagnetic ion and n is an integer that is 2 or greater. Benefits may be realized from the approach disclosed in the patent application over the "active visualization" technique method since it eliminates the need for the incorporation of RF coils and transmitting wires into the device and it provides visualization of the complete device and not merely the tip. However, this approach appears to be complex because of the necessity to engage in chemical grafting and plasma treatment. Further, it is believed to be extremely difficult to implement for a commercial-scale application.

Consequently, a simple coating process that is compatible with current hydrophilic, lubricious coating technology to impart such MRI capability to a medical device is desired in the art.

SUMMARY OF THE INVENTION

In accordance with the present invention, improved lubricious medical devices such as, for example, catheters, guide wires, endotracheal tubes, balloons and implants are provided. The medical devices of the present invention comprise a hydrophilic, lubricous coating and an agent which is magnetic susceptible. The agent is physically incorporated into the lubricious coating, or migrates from a polymeric matrix into the lubricious coating upon hydration.

By the present invention it is now possible to prepare devices that are both lubricious and visible in MR using easily controlled and simple manufacturing processes.

BRIEF DESCRIPTION OF THE DRAWING

FIG. 1 shows a comparison of spectra from an elemental analysis of a scanning electron microscope of an uncoated specimen and a coated specimen.

FIG. 2 shows a cross-section of a 7 french guide wire composed of a nylon-polyethylene copolymer with imbibed gadolinium salt.

FIG. 3 shows a cross-section of a nylon-polyethylene copolymer substrate coated with a gadolinium complex and overcoated with cellulose acetate.

DESCRIPTION OF THE INVENTION

The magnetic susceptible agents useful in accordance with the present invention can be any materials, elements or ions that have magnetic susceptibility, e.g., can produce a contrast in magnetic resonance imaging. Typical ingredients suitable for use in accordance with the present invention include, for example, paramagnetic ions, paramagnetic ion complexes and super-paramagnetic particles. A preferred magnetic susceptible agent is diethylenetriamine-pentaacetic acid gadolinium (III) dihydrogen salt. Other preferred magnetic susceptible agents include organometallic complexes, such as, but not limited to, tetrazazcyclotetradecane tetraacetic acid gadolinium complex and tetrazazcyclododecane tetraacetic acid gadolinium complex. Other preferred multivalent paramagnetic metals include, for example, iron, manganese, chromium, cobalt, and nickel. An especially preferred paramagnetic ion is gadolinium. Other suitable magnetic susceptible agents are disclosed, for example, by Jinkins J. R., America J. of Neuroradiology, 1992, 13, 19–27. Further details concerning the selection of suitable magnetic susceptible agents are known to those skilled in the art.

The lubricious polymers suitable for use in accordance with the present invention comprise any polymers which are substantially more lubricous when wetted with an aqueous liquid than when dried, e.g., as evidenced by a reduction in the coefficient of friction. Typically, the lubricious polymers have a water solubility of at least about 1.0 wt % and preferably at least about 2.0 wt. % or are water-swellable. As used herein, the term "water-swellable" means a substantially hydrophilic polymer which, even though is not soluble in water, would absorb sufficient water to render it lubricious in the hydrated state. In addition, the term "hydrophilic" as used herein means that water droplets do not readily form beads on the surface of such hydrophilic material, but instead the water droplets tend to assume a contact angle of less than 45° and readily spread on its surface. Further details concerning hydrophilic coatings which are useful for purposes of this invention are disclosed by Fan, Y. L. "Hydrophilic Lubricity in Medical Applications", Encyclopedia Handbook of Biomaterials and Bioengineering, edited by D. L. Wide, Part A, Vol. 2, p 1331.

Preferred hydrophilic polymers include, but are not limited to, those selected from the group consisting of polyvinyl compounds, polysaccharides, polyurethanes, polyacrylates, polyacrylamides, polyalkylene oxides, and copolymers, complexes, mixtures, and derivatives thereof. Poly(N-vinyl lactams) are preferred polyvinyl compounds for use in accordance with the present invention. The term "poly(N-vinyl lactam)" as used herein means homopolymers and copolymers of such N-vinyl lactams as N-vinyl pyrrolidone, N-vinyl butyrolactam, N-vinyl caprolactam, and the like, as well as the foregoing prepared with minor amounts, for example, up to about 20 weight percent, of one or a mixture of other vinyl monomers copolymerizable with the N-vinyl lactams. Of the poly(N-vinyl lactams), the poly(N-vinyl pyrrolidone) homopolymers are preferred. A variety of poly(N-vinyl pyrrolidones) are commercially available and of these a poly(N-vinyl pyrrolidone) having a K-value of at least about 30 is especially preferred. The K value is a measure of molecular weight, the details of which are known to those skilled in the art. Other preferred hydrophilic polymers for use in accordance with the present invention include, but are not limited to, those selected from the group consisting of N-vinylpyrrolidone-hydroxyethyl acrylate copolymers, carboxymethyl cellulose, hydroxyethyl cellulose, polyacrylamide, poly(hydroxyethyl-acrylate), cationically-modified hydroxyethyl cellulose, poly(acrylic acid), poly(ethylene oxides), and complexes, mixtures, and derivatives thereof. Especially preferred are poly(N-vinylpyrrolidone), poly(acrylic acid), poly(ethylene oxide) and cellulosics, such as, for example, carboxymethyl cellulose and cationically modified cellulose.

The lubricious polymers suitable for use in accordance with the present invention can be nonionic, cationic, anionic or amphoteric. Typically, the molecular weight of the lubricious polymers is from about 100,000 to 2,000,000,000 grams per gram mole, preferably from about 200,000 to 5,000,000 grams per gram mole, and, more preferably, from about 300,000 to 2,000,000 grams per gram mole. As used herein, the term "molecular weight" means weight average molecular weight. Methods for determining weight average molecular weight, e.g., light scattering, are known to those skilled in the art. Further details concerning the preparation and selection of lubricious polymers suitable for use in accordance with the present invention are known to those skilled in the art. Such lubricious polymers are readily commercially available from a variety of sources such as, for example, Union Carbide Corporation, Danbury, Conn.

Preferably, a binder polymer having functionality to promote bonding of the lubricious polymer to the medical device substrate is used in accordance with the present invention. Typical binder polymers comprise moieties which form a covalent bond between the binder polymer and the lubricious polymer, e.g., isocyanate, aldehyde or epoxy moieties, or those which primarily form a hydrogen or ionic bond, e.g, polymers which comprise a vinyl moiety, such as vinyl chloride or vinyl acetate and a carboxylic acid moiety. Further details of such binder polymers are known in the art and described for example in U.S. Pat. Nos. 5,091,205 issued Feb. 25, 1992 and 5,731,087 issued Mar. 24, 1998.

In addition to the binder polymers and lubricious polymers and magnetic susceptible agents, the lubricious coatings of the present invention may comprise one or more additives normally used in coating formulations such as, for example, surfactants, preservatives, viscosity modifiers, pigments, dyes, physiologically active agents and other additives known to those skilled in the art. Typical physiologically active ingredients include, for example, therapeutic agents, antithrombogenic agents, antimicrobial agents and antibiotic agents. When ionic additives are employed in the coating, e.g., heparin, which is anionic, it is preferred to use a cationic lubricious polymer, e.g., a cationically-modified hydroxyethyl cellulose. Similarly, when an additive is cationic, it is preferred to use an anionic lubricious polymer, e.g., a polyacrylic acid-acrylamide polymer. The combination of an additive and a lubricious polymer may be varied as needed to provide the desired performance.

The substrates having surfaces upon which the lubricious coatings of the present invention can be applied are not limited. The substances which are usable for the substrates include, but are not limited to, various organic polymeric compounds such as, for example, polyamides, polyesters, e.g., polyethylene terephthalate and polystyrene terephthalate, polyvinyl chloride, polyvinylidene chloride, polystyrene, polyacrylic esters, polymethylmethacrylate and other polymethacrylic esters, polyacrylonitrile, polyethylene, polypropylene, polyurethane, polyvinyl acetate, silicone resins, polycarbonate, polysulfone, polybutadiene-styrene copolymers, polyisoprene, nylon, polyethylene, polypropylene, polybutylene, halogenated polyolefins, various latexes, various copolymers, various derivatives and blends thereof. The substrates may also comprise, in addition to the substrate polymer, various inorganic and metallic substances such as, for example, glass, ceramics, stainless steel, and a super elastic metal or shape memory alloys such as Ni—Ti alloy, for example. Typical medical devices to which the lubricious coatings of the present invention can be applied include, but are not limited to, catheters, balloon catheters, guide wires, endotracheal tubes, implants and other medical devices.

The lubricious coatings of the present invention may be applied by either a two-step coating process or a one-step coating process. In a preferred two-step coating process, the portion of the substrate to be coated is first coated with the binder polymer and subsequently coated with the lubricious polymer. In a preferred one-step coating process, the binder polymer and lubricious polymer are applied to the substrate in a single step. Any conventional liquid coating processes may be utilized in accordance with the present invention. Such processes include, for example, dip-coating, spray-coating, knife-coating and roller coating. Dip-coating is a preferred coating method in accordance with the present invention.

In preferred coating processes of the present invention, the binder polymers and the lubricious polymers may be delivered from liquids contained in either a solution, a dispersion or an emulsion of the polymers, e.g., the binder polymer being applied in a first liquid medium and the lubricious polymer being applied in a second liquid medium. In the one-step coating methods, the binder polymers and the lubricious polymers are contained in the same, i.e., common liquid medium. In the two-step methods, the binder polymers and the lubricious polymers are contained in separate liquid mediums. Additional coating steps may also be employed to introduce different polymers or additives, e.g., the physiologically active ingredient as hereinafter described. The liquid mediums used for delivering the binder polymers and lubricious polymers may be organic, aqueous or an organic-aqueous mixture. The liquid medium used for delivering the binder polymer can be selected so that it has some solvency for the substrate, i.e., when the substrate is polymeric. This can enhance the adhesion between the binder polymer and the substrate and aid to the film formation of the coating material. Preferred liquid mediums for delivering the binder polymers and lubricious polymers include, but are not limited to, esters, e.g., ethyl acetate, isopropyl acetate, ethyl lactate; alcohols, e.g., isopropyl alcohol, ethanol, butanol; ketones, e.g., acetone, methylethylketone, diacetone alcohol, methyl isobutyl ketone; amides such as dimethyl formamide; toluene; glycol ethers such as butyl glycol ether; chlorinated solvents such as dichloroethane, water, and mixtures thereof. Preferably, the liquid mediums are selected so that the binder polymers and lubricious polymer evenly wet the surface of the substrate to be coated. The additives, when employed, may be contained in either or both of the liquid mediums containing the binder polymer or the lubricious polymer or may be contained in a separate liquid medium.

In a preferred aspect of the present invention, an additional coating can be applied to inhibit the diffusion of the magnetic susceptible agent out of the coating into body fluids. The additional coating is typically comprised of a coating agent, e.g., a polymer such as cellulose acetate, which is effective to inhibit the diffusion of the magnetic susceptible out of the hydrophilic coating. The selection, amount and application of the coating agent can be readily determined by those skilled in the art.

Preferably, the concentration of the binder polymer and the lubricious polymers in the liquid mediums are sufficient to provide the desired amounts of the respective polymers in the lubricious coatings. Typically, the concentration of the binder polymers in the liquid medium will range from about 0.05 to 10 weight percent and, preferably, from about 0.2 to 2 weight percent based on the total weight of the liquid medium. Typically, the concentration of the lubricious polymers will range from about 0.1 to 20 weight percent and, preferably, from about 0.5 to 5 weight percent, based upon the total weight of the liquid medium. Further details concerning the selection of liquid mediums for delivering the binder polymers and lubricious polymers of the present invention are known to those skilled in the art. The concentration of additives in the liquid medium is dependent on the particular additive and desired effect and can be determined by those skilled in the art.

The coating processes of the present invention are preferably conducted in a liquid phase at atmospheric pressure and at a temperature from about 20 to 90° C. The residence times for contacting the surface of the substrate to be coated with the liquid mediums containing the binder polymer or the lubricious polymer, or both, range from about 1 second to 30 minutes, preferably from about 5 seconds to 10 minutes. It is generally desirable to dry the coatings after application of the coating at a temperature from about 30 to 150° C., preferably in a forced-air oven. Microwave ovens, vacuum ovens and infrared heaters may also be used if desired. Typical drying times range from about 1 minute to 24 hours and preferably range from about 10 minutes to 10 hours. When a two-step coating process is employed, it is preferred to dry the binder polymer before application of the lubricious polymer.

Preferably in accordance with the present invention, the process is conducted with a substantial absence of a plasma treatment step such as described in PCT patent application publication number WO 99/60920. More preferably, there is no plasma treatment in the processes of the present invention.

The lubricious coatings that result from the coating processes of the present invention typically have a thickness of from about 0.05 to 20 microns, and preferably from about 0.1 to about 10 microns. When a two-step coating process is employed, the resulting coating preferably comprises an inner layer that is rich, i.e., greater than 50%, in the binder polymer which contacts the surface of the substrate, and an outer layer which is rich, i.e., greater than 50%, in the lubricious polymer which contacts the inner layer. The outer layer, which is rich in the lubricious polymer, has an outer surface that becomes lubricious when exposed to an aqueous or organic liquid. When a one-step coating process is employed, the resulting coating comprises a single layer that is preferably a substantially homogeneous mixture of the binder polymer and the lubricious polymer. However, since the binder polymer will often have more affinity for the substrate than the lubricious polymer, it is believed that there may be a higher concentration of the binder polymer within or near the surface of the substrate.

The particular manner in which the magnetic susceptible agents is incorporated into the coating is not critical to the present invention. In a preferred aspect of the invention, in order to incorporate the magnetic susceptible agents into the coating of the substrate, a gadolinium complex is added into one or more of the liquid mediums in which the device is dipped. The liquid medium, e.g., third liquid medium, is preferably an aqueous solution or dispersion containing a water-soluble or water-dispersible paramagnetic compound. The preferred aqueous solutions are those containing either an inorganic salt such as sodium phosphate or a water-soluble polymer such as poly(N-vinyl pyrrolidone), or both. The dipping step is preferably followed by drying either in air, an oven, or any other suitable heat-generation source. This coating process may be repeated as necessary until sufficient loading of the paramagnetic compound is deposited on the surfaces of the medical device. Alternatively, the paramagnetic compound may be dissolved or suspended in the coating solution and the paramagnetic compound is deposited on or impregnated in the polymeric matrix of the medical device. Furthermore, the paramagnetic compound may be deposited on or impregnated in the medical device by a separate coating step from an aqueous medium containing a water-miscible organic solvent.

In another aspect of the invention, the magnetic susceptible agents is imbibed into the surface of the medical device. In order to imbibe the magnetic susceptible agents into the medical device in accordance with the processes of the present invention, a polymeric substrate having a matrix with (i) an internal region comprising a substrate polymer (as described above) and (ii) an outer surface is contacted with a liquid medium (as described above) having solvency for the substrate polymer. As used herein, the term "solvency" means that the liquid medium is a solvent for the substrate polymer (at the coating temperature) or is effective to promote swelling of the substrate polymer. The contacting can be conducted prior to, simultaneously with or after the application of the lubricious polymer to the polymeric substrate. Preferably, the contacting with the liquid medium comprising the magnetic susceptible agents is conducted prior to the application of the lubricious polymer. As used herein the term "imbibing" means to cause the transport of the magnetic susceptible agents from the liquid medium to the internal region of the matrix of the substrate polymer. The liquid medium comprises an effective concentration of the magnetic susceptible agents to promote the imbibing of the magnetic susceptible agents into the matrix of the substrate polymer.

The imbibing process is typically carried out at atmospheric pressure, and at a temperature of from about 20 to 90° C. by dipping, spraying, rolling or otherwise contacting the polymeric substrate in the liquid medium for a relatively short duration such that there is preferably no more than a 10% change, more preferably no more than a 7% change in either the longitudinal or horizontal dimension or shape upon drying of the polymeric substrate. Preferably, the cross-sectional dimension, e.g., diameter of a catheter, evidences no more than a 10% change in the cross-sectional dimension after contacting with the liquid medium as compared to the cross-sectional dimension prior to said contacting. The resulting imbibed substrate can be dried as described above either before or after applying the lubricious coating.

In another aspect of the invention, the polymeric substrate and the magnetic susceptible agent are coextruded to form a molded element which comprises a portion or all of the medical device. After extrusion, the medical device can be coated with lubricious polymers as described above. Further details concerning the conditions for extrusion and apparatus for extrusion are known to those skilled in the art.

The loading of the paramagnetic compound in the lubricious coating is governed by the $T_1$ relaxation time of the water molecules in the coating. In general, a sufficient loading, i.e., concentration, of the paramagnetic compound is required to reduce the $T_1$ relaxation time by at least 10%, preferably 50% and more preferably 90% of the background such that a reasonably clear MRI can be obtained. The percent loading is controlled by the concentration of the paramagnetic compound in the solution or dispersion, the length of dipping time, and the number of coats applied. These operating conditions can be readily chosen by those who are skilled in the art for a given substrate material, a given paramagnetic compound and for a specific application. Further details concerning the loading required for a particular situation can be determined by one skilled in the art.

EXAMPLES

The following examples are provided for illustrative purposes and are not intended to limit the scope of the claims that follow.

In the following examples, in order to measure relaxation effects in the magnetic field, inversion-recovery experiments were conducted using nuclear magnetic resonance (NMR). An inversion-recovery experiment is a standard method for determining the spin-lattice relaxation time $T_1$. In this experiment, the sample is pulsed 180° in the x direction. The evolution of the magnetization vector is followed as magnetization vector relaxes back to realignment with the applied magnetic field in the z direction).

The equation to find $T_1$ is the following:

$$M_o - M_z = A \; e^{-t/T1}$$

Mz is the magnetization in the z-direction at the time t; A is a constant whose value depends on initial conditions.

The effect of super-paramagnetic particles on spin-spin relaxation time is detected by measuring the line width of the observed NMR signals. In fact, since shortening either longitudinal or transverse relaxation time results in the broadening of the signal, this is a good screening tool to observe whether an agent will be visible in MR.

Example 1

This example illustrates the incorporation of a paramagnetic ion into the coating of a medical device. The polymeric device used was a 7 french guidewire that is constructed of a nylon/polyethylene copolymer. The guidewire was cut into nine inch samples, cleaned with isopropanol, and air-dried. The specimens were dipped into the bath containing P-106 primer solution (a polyisocyanate available from Union Carbide Corporation of Danbury, Conn.) for 15 minutes. After dipping they were placed in a preheated forced air oven at 65° C. for 20 minutes. Thereafter, stents were removed from the oven and dipped in another coating bath containing POLYSLIP™ COATING T-503M (a dispersion of poly(acrylic acid) in a solvent mixture of dimethyl formamide, t-butyl alcohol, and methyl ethyl ketone available from Union Carbide Corporation of Danbury, Conn.) for 10 seconds and followed by drying at 65° C. for 2 hours. The coated stents were further dipped in an aqueous sodium phosphate bath that contained 10% diethylenetriamine-penta-acetic acid, gadolinium (III) dihydrogen salt hydrate for 10 minutes and dried at 65° C. for 11 hours. The finished coating was smooth and uniform. Three devices were treated. Both SEM and ESCA detected gadolinium on the surface of each of the specimens (FIG. 1). Results from the inversion-recovery experiment were that all three samples reduced the $T_1$ relaxation time of degassed water from 7 seconds to 0.3–0.7 seconds. Uncoated samples had no significant effect on the proton $T_1$ relaxation time.

Example 2

This example illustrates the incorporation of a paramagnetic ion into a polymeric matrix. Kraton G, a styrene-butadiene copolymer (30 g) powder was mixed with 49 g of Ferumoxsil Oral Suspension (Mallinckrodt Medical). Ferumoxsil is a liquid formulation that includes iron oxide nanoparticles that is usually used for MR imaging of the GI tract. The concentration of iron in the formulation is 175 microgram/mL. Due to the propensity of the iron oxide particles to settle, the Ferumoxsil was mixed with an overhead mixer before addition to the polymer powder. The mixture was blended for 5 minutes in a Waring blender at the lowest speed. The mixture was placed in a crystallization dish, covered with a Kimwipe and dried in a vacuum oven at 110° C. overnight.

The resulting brown mixture (6 g) was placed in a stainless steel mold and mold was placed in a Greenard press. The platens were heated to 180° C. and the mixture was pressed for 2 minutes at this temperature. Plaque was quench cooled by running ambient water through the press.

Samples of the plaque as well as a control plaque of Kraton G with no additives were screened for effects in a magnetic field using NMR. The plaque with Ferumoxsil showed a broader signal in the NMR relative to the control plaque. The linewidth of the sample signal was 60 Hz and the linewidth of the reference sample was 50 Hz. The effect on the magnetic field between the two samples was evident.

In addition, to further explore the super-paramagnetic effect, nanoparticles of iron oxide were extruded into polyethylene. Five (5) g of iron oxide (average 30 nm in size) particles were mixed with 20 g of polyethylene resin and extruded into polyethylene resin. The extruded sample was analyzed by NMR and compared to that of neat extruded polyethylene resin. The spectra of the sample containing the iron oxide nanoparticles demonstrated a complex shape with the nominal line width of approximately 276 Hz. Moreover, some components demonstrated even more pronounced broadenings, and the width at 10% of the height was 2 kHz. The control sample increased the line width only slightly to 15 Hz. The signal of water itself under applied experimental conditions was broadened only to 8 Hz.

The extruded polyethylene sample containing the iron oxide nanoparticles was coated using the procedure and materials described in Example 1, but omitting the gadolinium complex, and subsequently analyzed by NMR for effect on the magnetic field. Quite surprisingly, the coating did not reduce the effect of the sample on the magnetic field. NMR results demonstrated the line width at half height was 460 Hz and the width at 10% of the height is 2.4 kHz.

Example 3

This example illustrates that different concentrations of the paramagnetic ion in dipping solution can be used to impart visibility in MR. The polymeric device used was a 7 french guidewire that is constructed of a nylon/polyethylene copolymer. The guidewire was cut into nine inch samples, cleaned with isopropanol, and air-dried. The specimens were dipped into a bath containing primer solution, P-106 for 15 minutes. After dipping they were placed in a preheated forced air oven at 65° C. for 20 minutes. Thereafter, stents were removed from the oven and dipped in another coating bath containing POLYSLIP™ COATING T-503M for 10 seconds and followed by drying at 65° C. for 2 hours. The coated stents were further dipped in an aqueous sodium phosphate bath that contained either 5 or 10% diethylenetriamine-penta-acetic acid, gadolinium (III) dihydrogen salt hydrate for 10 minutes and dried at 65° C. for 11 hours. The finished coating was smooth and uniform. NMR investigation indicated that both types of stents shortened the $T_1$ relaxation time of water protons from 7 sec to 0.1 s and 0.4 s, respectively.

Example 4

This example illustrates that a sufficient concentration of super-paramagnetic particles on the surface of a substrate results in a dramatic perturbation of the magnetic field. This example illustrates the incorporation of a paramagnetic ion into the coating of a medical device. The polymeric device used was a 7 french guidewire that is constructed of a nylon/polyethylene copolymer. The guidewire was cut into nine inch samples, cleaned with isopropanol, and air-dried. The specimens were dipped into the primer solution, P-106, for 15 minutes. After dipping they were placed in a preheated forced air oven at 65° C. for 20 minutes. Thereafter, stents were removed from the oven and dipped in another coating bath containing POLYSLIP™ COATING T-503M for 10 seconds and followed by drying at 65° C. for 2 hours. The coated stents were dipped in the Ferumoxsil Oral Suspension for 10 minutes and then air dried for 10 minutes. This last dipping step was repeated 6 times.

Example 5

This example illustrates the effect of an increase in the concentration of iron oxide particles on the surface of a polymeric substrate. Standard T60 videotape made by 3M was wrapped around a 2 mm thick 5 cm long plastic tube and analyzed as described above. The resulting linewidth of the water protons was increased to 700 Hz relative to the 40 Hz associated with the unwrapped tube. This result indicates that dramatic effects to the applied magnetic field can be obtained if sufficient of the super-paramagnetic particles can be immobilized on the surface of a substrate. Coatings of super-paramagnetic particles can be obtained by dip-coating, powder coating, coextrusion and laminating. The videotape-wrapped tube is an illustration of the feasibility of this technology.

Example 6

This example illustrates that a paramagnetic compound can also be imbibed in a polymeric matrix of a medical device from an organic solution. The water-soluble paramagnetic compound will migrate from the polymeric matrix to the hydrated layer of the hydrophilic coating to produce an image in magnetic resonance. Two pieces of 6 French (ethylene-vinyl acetate) copolymer stents are impregnated in a pyridine solution containing 2.5% of the gadolinium-diethlenetriamine pentaacetic acid complex and 2% of distilled water for a period of 1 hour at room temperature. The stents are air-dried for 1 hour at room temperature. The stents are subsequently coated with a hydrophilic, lubricious coating using a procedure similar that in Example 1 with the exception that there is no additional gadolinium complex added to the sodium phosphate solution. The finished stents are covered uniformly with a layer of hydrophilic coating.

Similarly, in another experiment a 7 french guidewire constructed of a nylon/polyethylene copolymer was incubated in a DMF/$GdCl_3$ solution and heated to 50° C. for 30 minutes. In this manner the imbibing of the Gd3+ ion into the matrix of the stent was achieved (see FIG. 2). NMR analysis of these samples after coating with the procedure and materials described in Example 1 showed that samples formulated in this manner reduced the T1 relaxation time of water from 3.5 seconds to 1.9 seconds. Moreover, the effect of the sample on the magnetic field of the instrument was maintained for 4 hours.

Example 7

This example illustrates that the length of time that the coated device has contrast in the magnetic field can be controlled. Since the gadolinium complexes or salts are readily water-soluble there is a tendency for them to diffuse out of the hydrophilic coating and into the surrounding environment. In order to reduce the rate of the diffusion into the surrounding environment a cellulose acetate coating was placed on the specimen (see FIG. 3). This was accomplished in the following way. A 4% (w/v) cellulose acetate/acetone solution was prepared. The gadolinium coated specimen (as prepared in Example 1) was dipped into the cellulose acetate solution at ambient temperature. Especially effective was a multiple dipping cycle with an air drying step in between each dip step. Samples prepared in this manner reduced the relaxation time of water from 3.7 seconds to below 1 second. Moreover this effect was maintained for approximately 100 minutes.

While the present invention has been described and exemplified with some specificity, those skilled in the art will appreciate the various modifications, including variations, additions, and omissions, that may be made in what has been described. For example, substances other than those specifically disclosed that can perturb the magnetic field can replace the paramagnetic ion. Moreover, the magnetic susceptible agents can be either incorporated into the hydrophilic lubricious coating by any of the suitable processes described above or by mixing within the polymeric matrix of the medical device. For instance, if the medical device is a catheter or stent the mixing may be achieved by using either an extruder or injection molding machine. Accordingly, it is intended that these modifications also be encompassed by the present invention and that the scope of the present invention be limited solely by the broadest interpretation that can lawfully be accorded the appended claims.

It is claimed:

1. A process for making a lubricious medical device capable of being detected by magnetic resonance imaging, said process comprising:
    (a) contacting a surface of the device with (i) a binder polymer; and (ii) a hydrophilic polymer selected from the group consisting of poly(N-vinyl lactams), polysaccharides, polyacrylates, polyacrylamides, polyalkylene oxides, and copolymers and mixtures thereof; and
    (b) contacting the surface with an effective amount of a magnetic susceptible agent to cause the surface of the medical device to be detectable by magnetic resonance imaging and the process is conducted in the substantial absence of plasma treatment.

2. The process of claim 1 wherein the surface is contacted with a first liquid medium comprising the binder polymer and subsequently contacted with a second liquid medium comprising the hydrophilic polymer.

3. The process of claim 2 further comprising drying the surface prior to contacting with the second liquid medium.

4. The process of claim 2 wherein the magnetic susceptible agent is comprised in at least one of the first liquid medium or the second liquid medium.

5. The process of claim 2 further comprising contacting the surface with a third liquid medium comprising the magnetic susceptible agent.

6. The process of claim 1 wherein the surface is contacted with a common liquid medium comprising the binder polymer and the hydrophilic polymer, and optionally the magnetic susceptible agent.

7. The process of claim 6 further comprising drying the surface after contacting with the common liquid medium.

8. The process of claim 1 wherein the magnetic susceptible agent is imbibed into the surface of the medical device.

9. The process of claim 1 wherein the magnetic susceptible agent has a paramagnetic ion.

10. The process of claim 9 wherein the magnetic susceptible agent has a paramagnetic ion selected from the group consisting of iron, manganese, chromium, cobalt, nickel and gadolinium.

11. The process of claim 1 wherein the magnetic susceptible agent is an organometallic complex.

12. The process of claim 11 wherein the magnetic susceptible agent is selected from the group consisting of diethylenetriamine-pentaacetic acid gadolinium (III) dihydrogen salt, tetrazacyclododecane tetraacetic acid gadolinium complex, tetrazazcyclotetradecane tetraacetic acid gadolinium complex, and mixtures thereof.

13. The process of claim 1 wherein the magnetic susceptible agent is selected from the group consisting of superparamagnetic particles and iodine containing contrast agents.

14. The process of claim 1 wherein the substrate is selected from the group consisting of polyurethane, polyvinyl chloride, polyacrylate, polycarbonate, polystryrene, polyester resins, polybutadiene-styrene copolymers, nylon, polyethylene, polypropylene, polybutylene, silicon, polyvinyl acetate, polymethacrylate, polysulfone, polyisoprene, and copolymers thereof, glass, metal, ceramic and mixtures thereof.

15. The process of claim 1 wherein the hydrophilic polymer is selected from the group consisting of polyN-vinylpyrrolidone, polyN-vinylpyrrolidone copolymers, carboxymethylcellulose, polyacrylic acid, cationically-modified hydroxyethylcellulose, polyethylene oxides, polyacrylamides and copolymers, and mixtures thereof.

16. The process of claim 15 wherein the binder polymer comprises an isocyanate, aldehyde, epoxy, vinyl or carboxylic acid moiety.

17. A process for making a lubricious medical device comprising a molded element capable of being detected by magnetic resonance imaging, said process comprising extruding a polymer in the presence of a magnetic susceptible agent to form the molded element; said molded element having a surface which is detectable by magnetic resonance imaging, and contacting a surface of the molded element with (i) a binder polymer; and (ii) a hydrophilic polymer selected from the group consisting of poly(vinyl lactams), polysaccharides, polyacrylates, polyacrylamides, polyalkylene oxides, and copolymers and mixtures thereof.

18. A medical device capable of being detected by magnetic resonance imaging, said device comprising:
    (a) a polymeric substrate having a matrix with (i) an internal region comprising a substrate polymer; and (ii) an outer surface; and
    (b) a layer of a hydrophilic polymer affixed to the outer surface, said hydrophilic polymer being selected from the group consisting of poly(N-vinyl lactanis), polysaccharides, polyacrylates, polyacrylamides, polyallcylene oxides, and copolymers and mixtures thereof wherein the hydrophilic polymer comprises a magnetic susceptible agent detectable by magnetic resonance imaging.

* * * * *